(12) United States Patent
Lee et al.

(10) Patent No.: US 8,110,642 B2
(45) Date of Patent: Feb. 7, 2012

(54) SYNTHESIS OF VINYLPHENYLPYRIDINE AND LIVING ANIONIC POLYMERIZATION

(75) Inventors: Jae-Suk Lee, Gwangju (KR); Nam-Goo Kang, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 386 days.

(21) Appl. No.: 12/227,140

(22) PCT Filed: Apr. 3, 2007

(86) PCT No.: PCT/KR2007/001631
§ 371 (c)(1),
(2), (4) Date: Jan. 2, 2009

(87) PCT Pub. No.: WO2007/129810
PCT Pub. Date: Nov. 15, 2007

(65) Prior Publication Data
US 2009/0105416 A1    Apr. 23, 2009

(30) Foreign Application Priority Data
May 8, 2006 (KR) .......................... 10-2006-0041121

(51) Int. Cl.
*C08F 26/06* (2006.01)
(52) U.S. Cl. ........................................ 526/265; 546/101
(58) Field of Classification Search .................. 526/265; 546/101
See application file for complete search history.

(56) References Cited

FOREIGN PATENT DOCUMENTS
JP        2005-298733     10/2005
WO    WO 2006/001150    1/2006

*Primary Examiner* — Edward Cain
(74) *Attorney, Agent, or Firm* — Harness, Dickey & Pierce, P.L.C.

(57) ABSTRACT

Provided are a vinyl-biphenylpyridine monomer and a polymer thereof. More particularly, the present invention provides a vinyl-biphenylpyridine monomer having a side chain of pyridine or phenylpyridine as a functional group, a homopolymer of which molecular weight and molecular weight distribution are controlled using the monomer, and a block copolymer of which molecular structure and molecular weight are controlled to facilitate synthesis of an organic metal complex. Accordingly, the present invention provides a vinyl-biphenylpyridine monomer and a polymer thereof which are effectively used as nano and optical functional materials.

8 Claims, 9 Drawing Sheets

[Fig. 1]
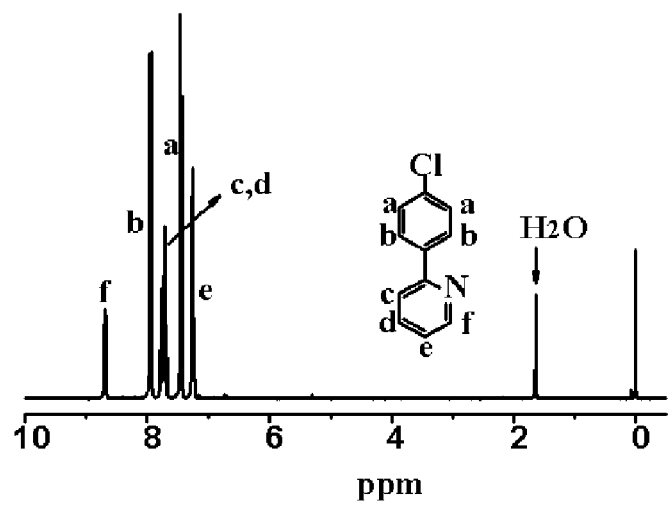
[Fig. 2]
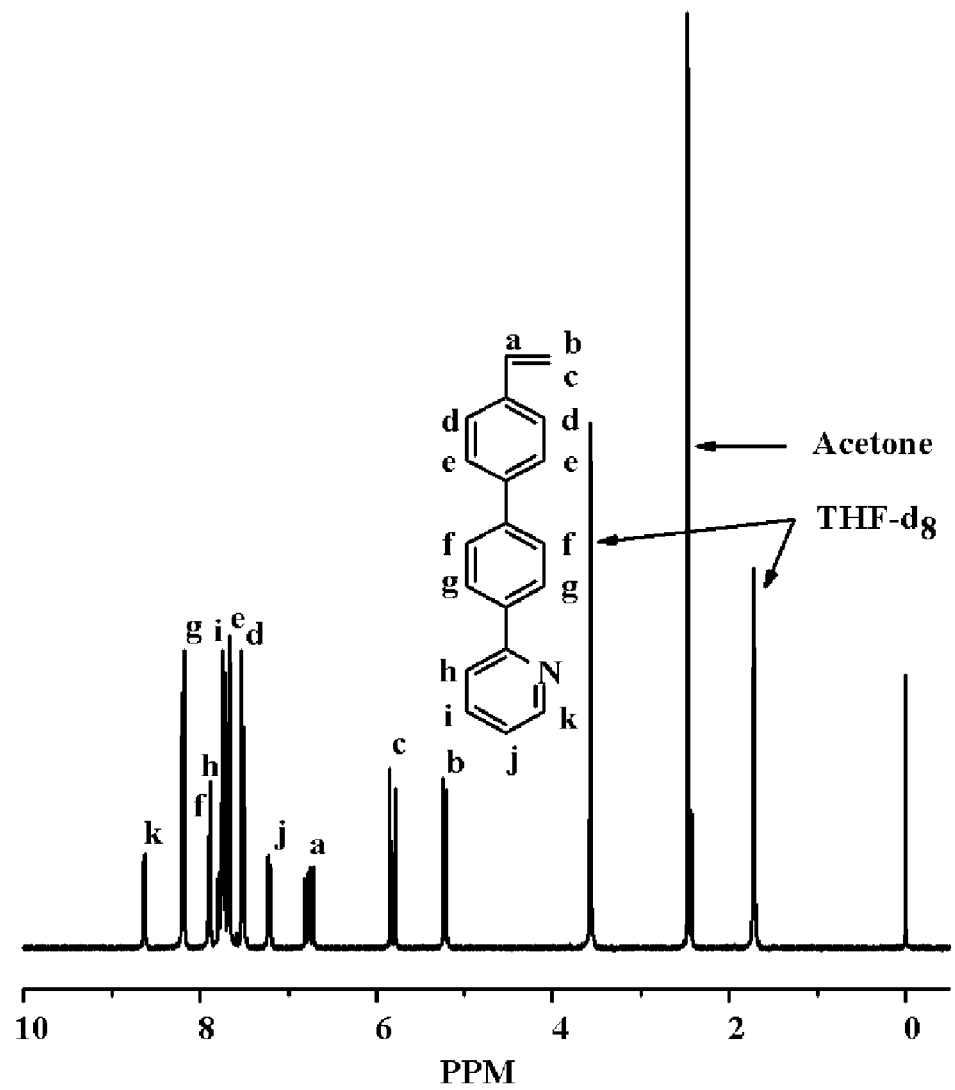

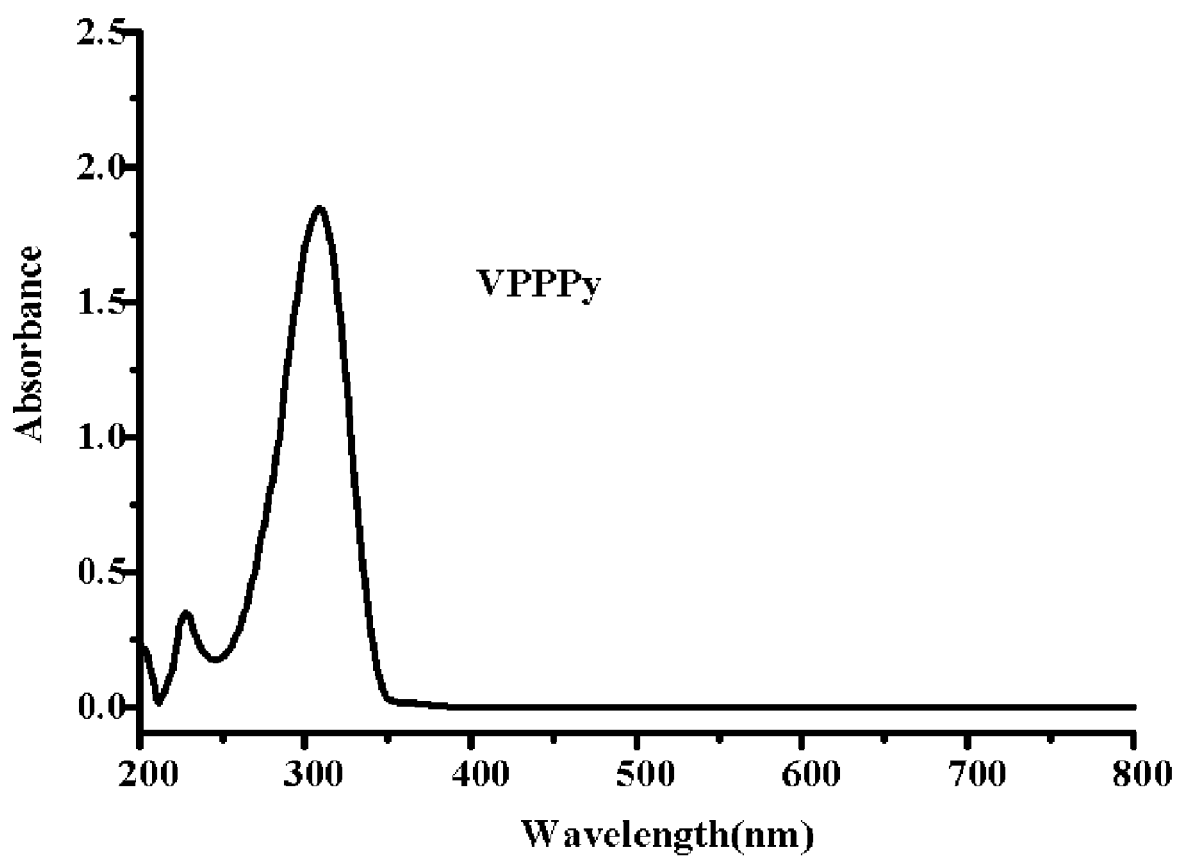
[Fig. 3]

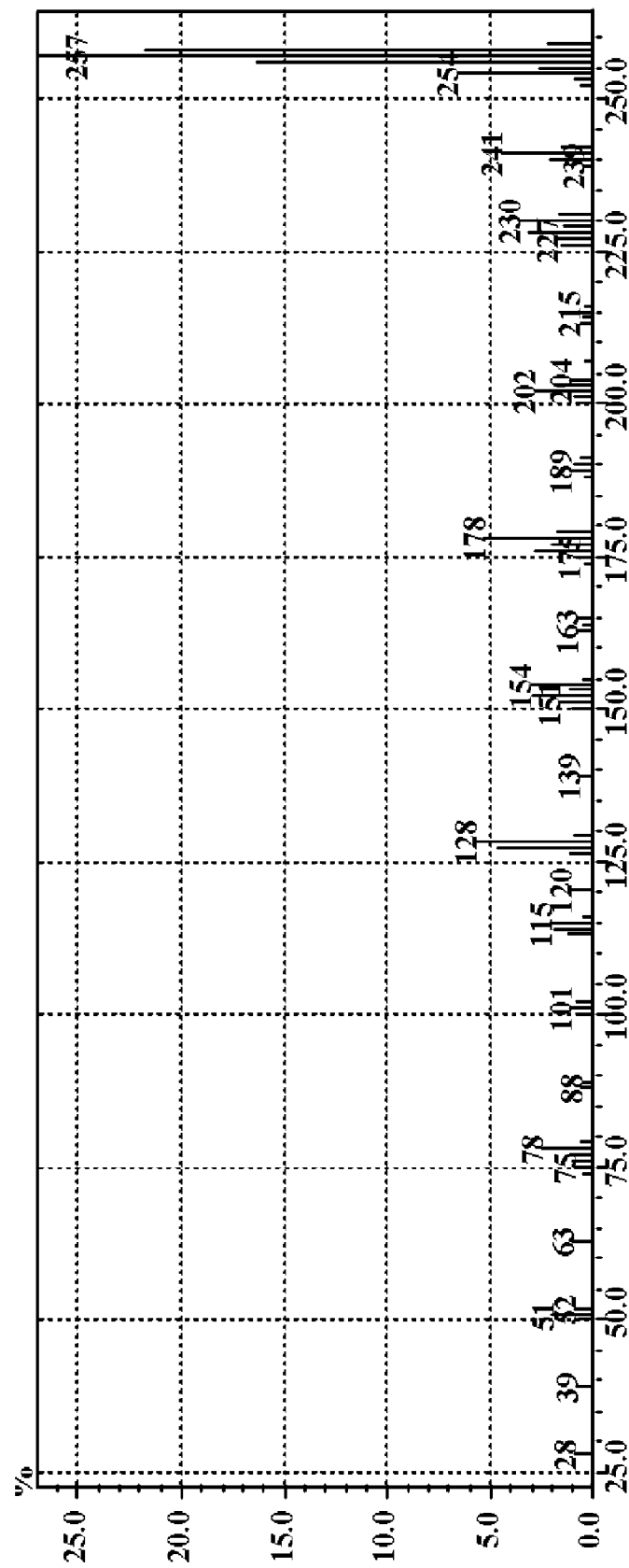
[Fig. 4]

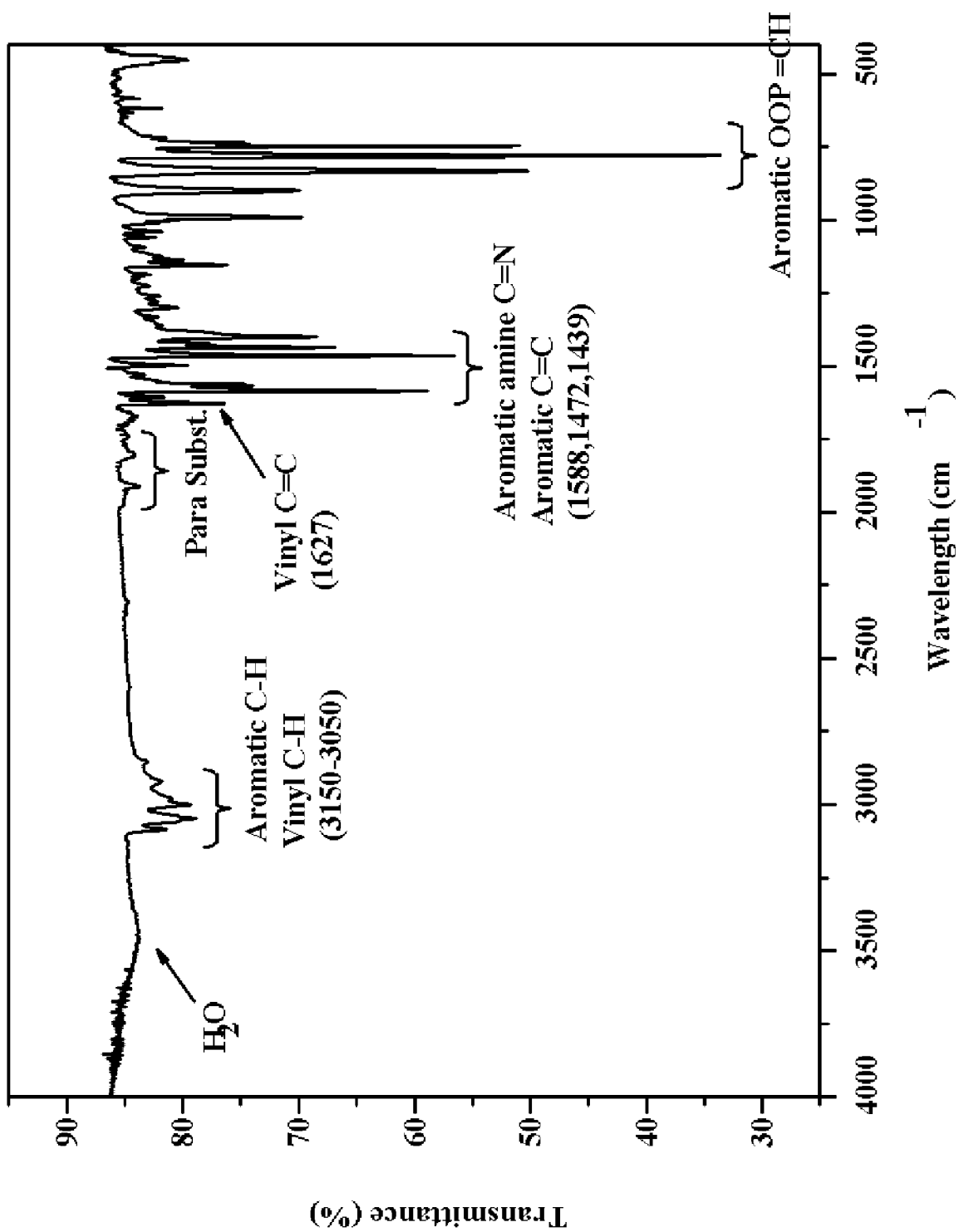
[Fig. 5]

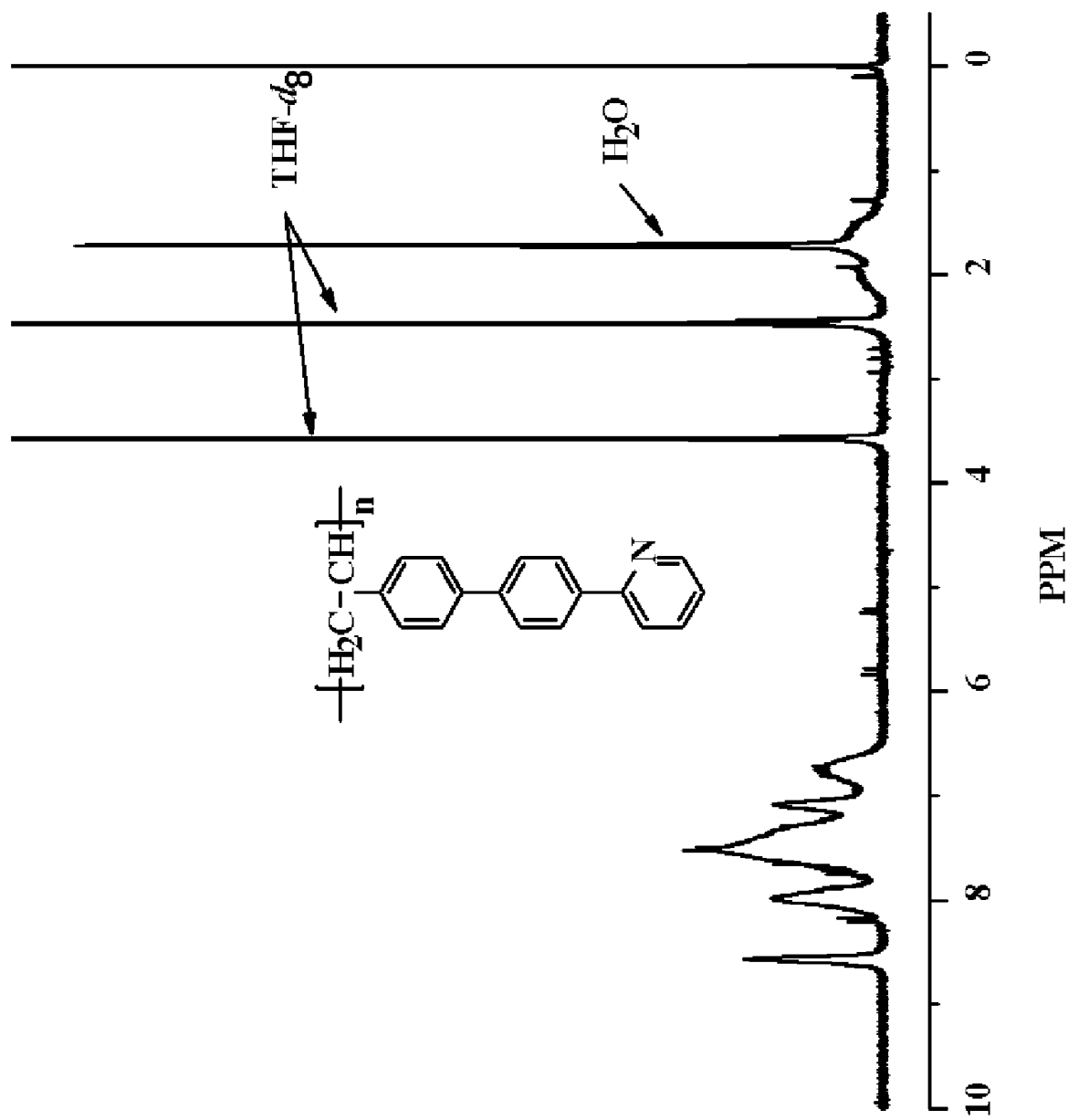
[Fig. 6]

[Fig. 7]
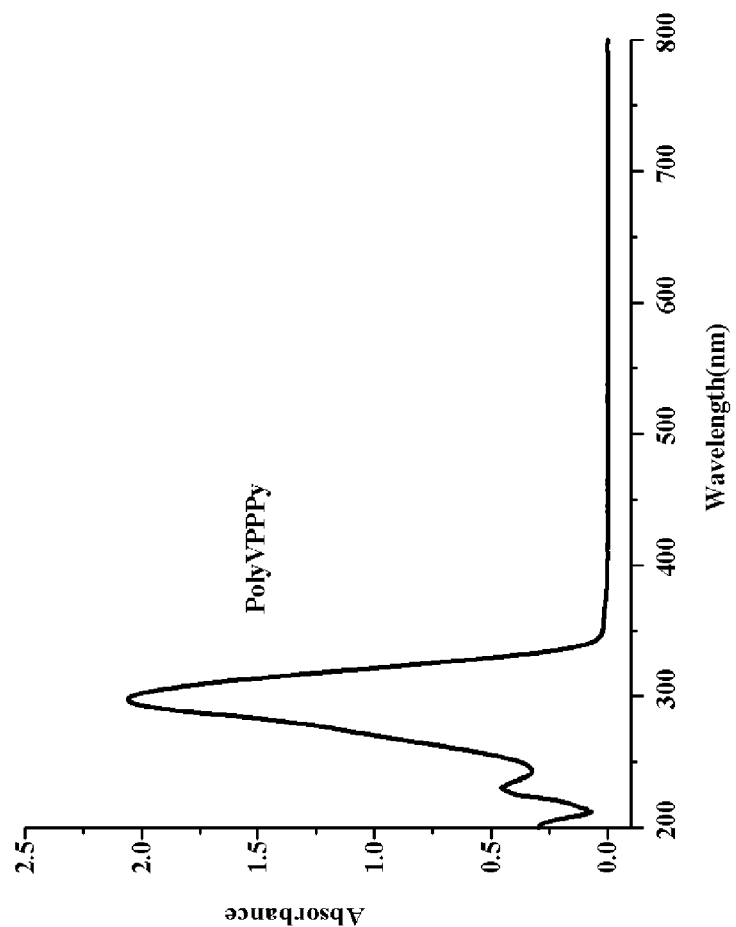
[Fig. 8]
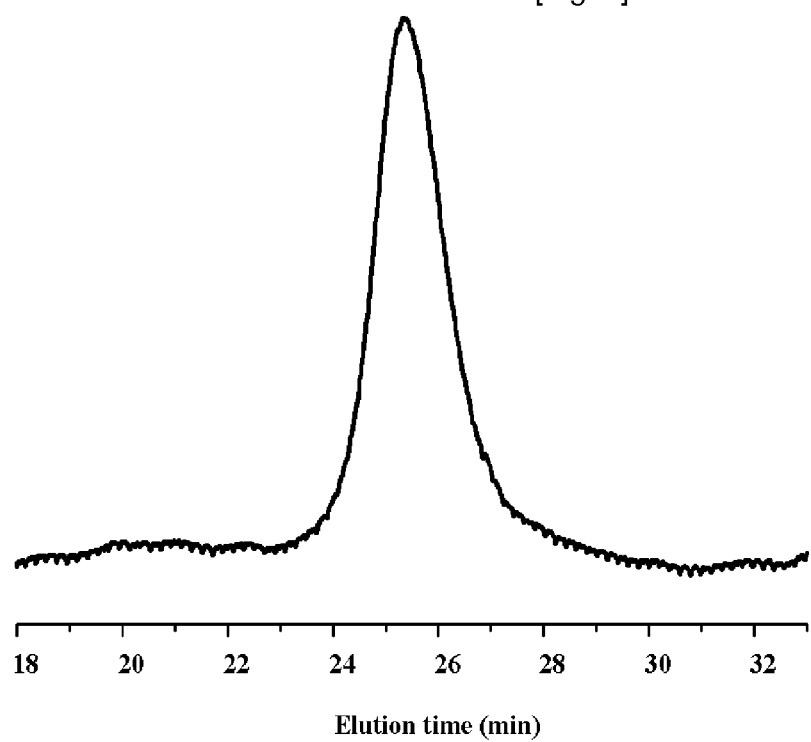

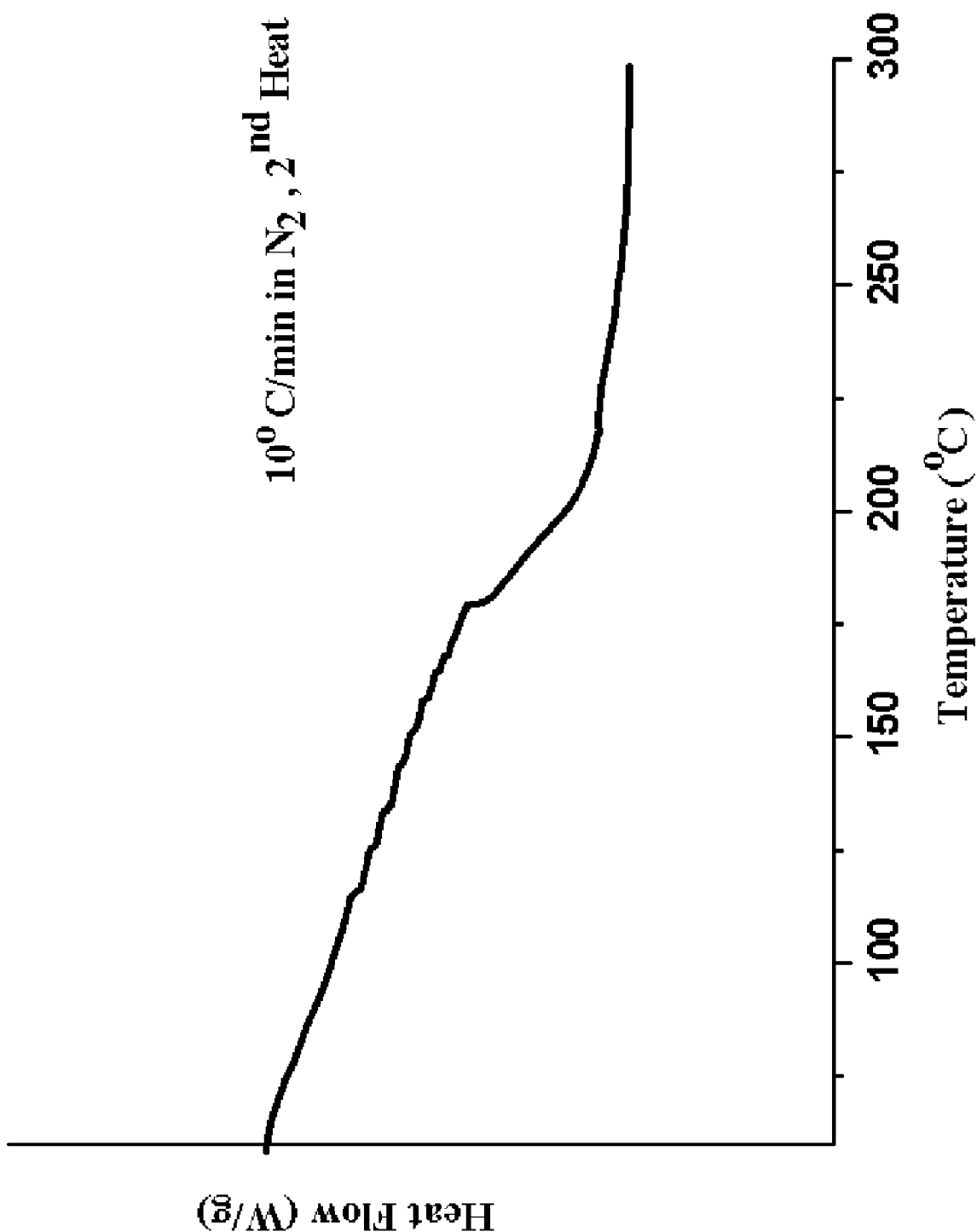
[Fig. 9]

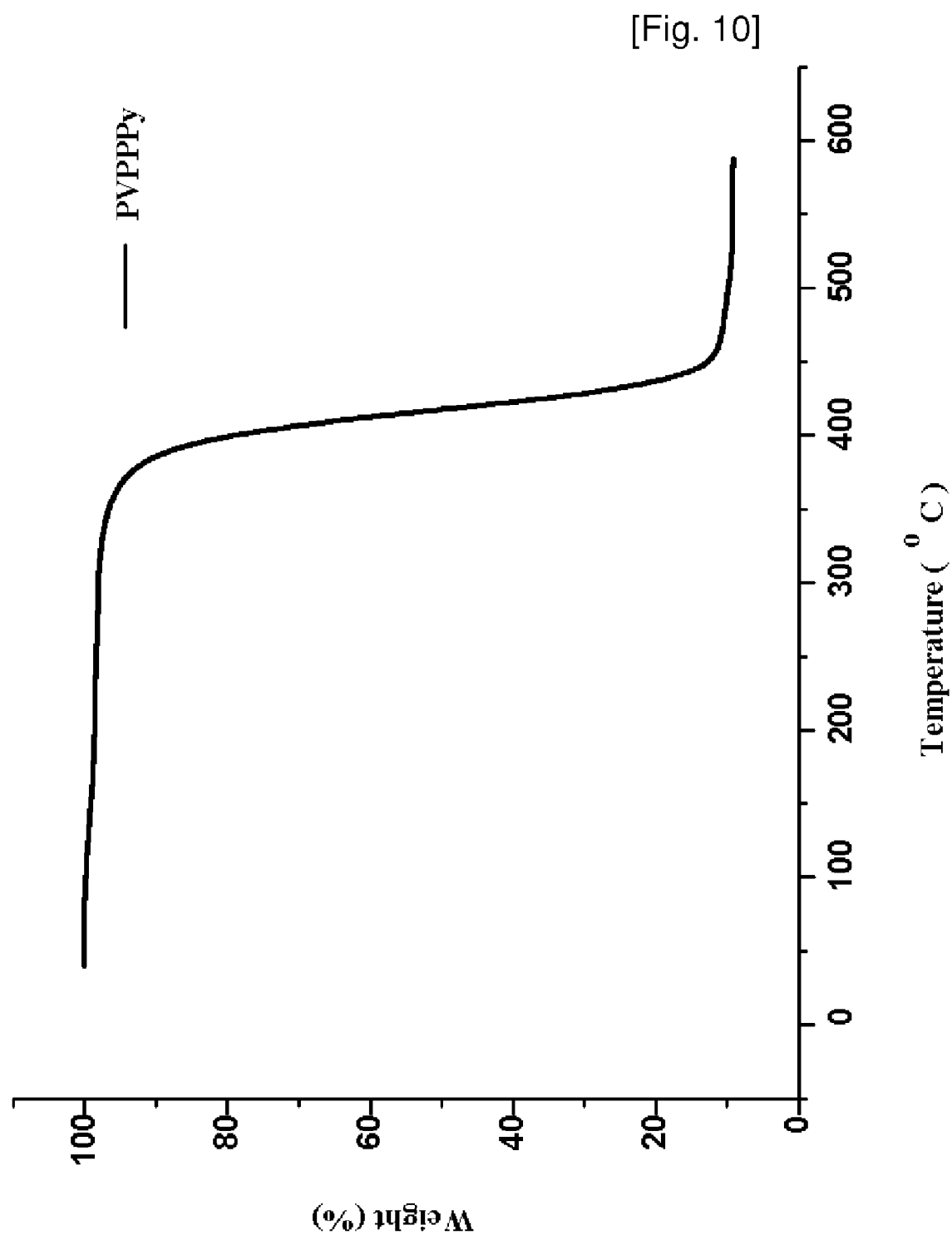
[Fig. 10]

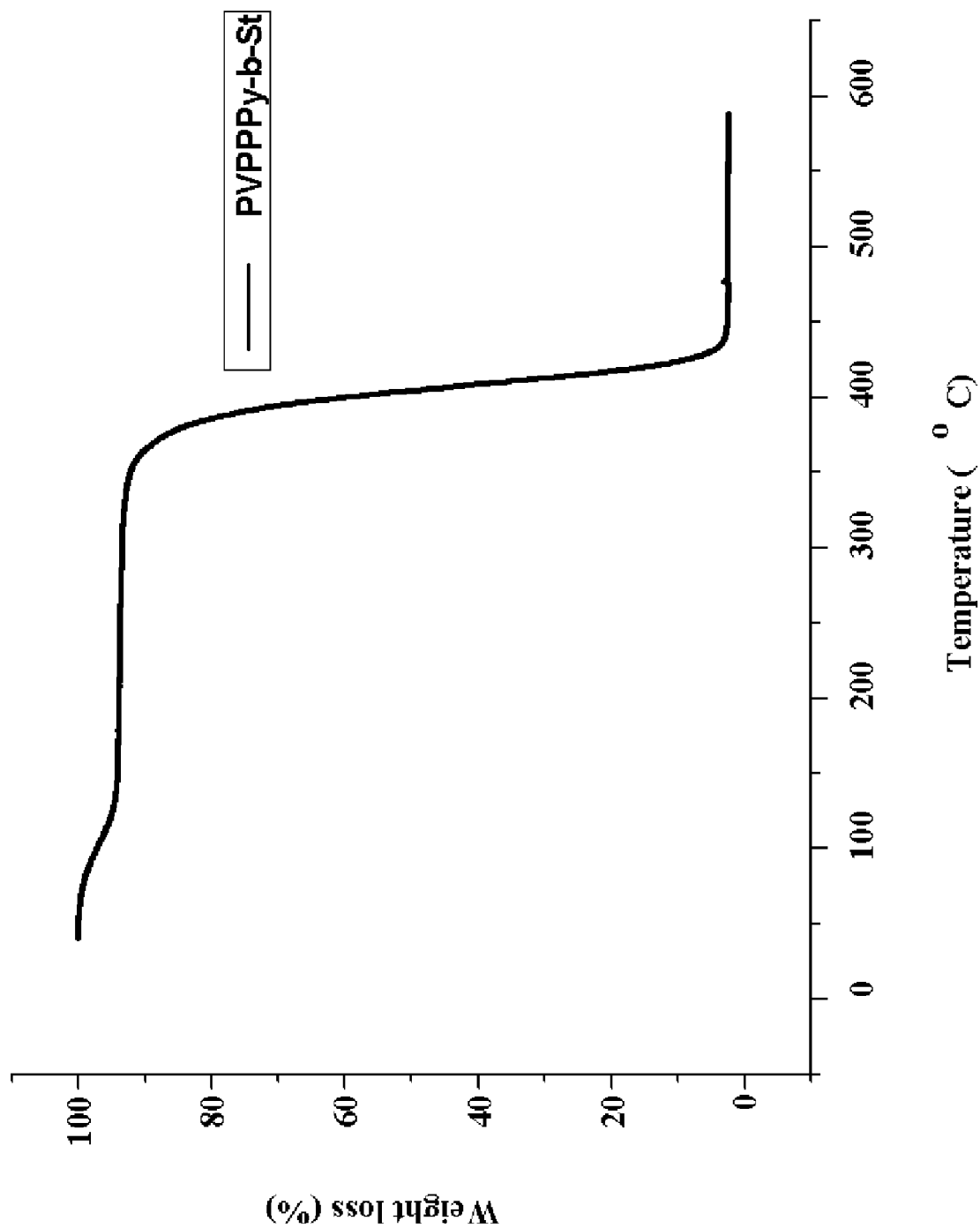
[Fig. 11]

SYNTHESIS OF VINYLPHENYLPYRIDINE AND LIVING ANIONIC POLYMERIZATION

PRIORITY STATEMENT

This application is a National Phase entry of PCT Application No. PCT/KR2007/001631, filed on Apr. 3, 2007, which claims priority to Korean Application No. 10-2006-0041121, filed on May 8, 2006.

TECHNICAL FIELD

The present invention relates to a vinyl-biphenylpyridine monomer and a polymer thereof and, more particularly, to a vinyl-biphenylpyridine monomer having a side chain of pyridine or phenylpyridine as a functional group, a homopolymer of which molecular weight and molecular weight distribution are controlled using the monomer, and a block copolymer of which molecular structure and molecular weight are controlled to facilitate synthesis of an organic metal complex. Accordingly, the present invention provides a vinyl-biphenylpyridine monomer and a polymer thereof which are effectively used as nano and optical functional materials.

BACKGROUND ART

Styrene monomers are capable of radical, cationic and anionic polymerizations owing to a resonance effect of a phenyl group thereof, differently from the other monomers. Moreover, since synthesized polystyrene polymers may be easily reformed and have excellent formability characteristics, the styrene monomers have been widely studied and thus commercialized.

Numerous researches on the styrene monomers have continued to progress since an anionic polymerization of styrene was developed. Moreover, since the styrene monomer having a functional group such as a hydroxy group, an amine group, a sulfur group, and the like causes various side reactions during the polymerization process due to a strong reactivity of an activated carbanion, various researches aimed at solving the problem have also continued to progress.

For example, a method of anionically polymerizing a styrene derivative having an electron donating group such as —CN, —$NO_2$, —$COCH_3$, —COOBut, —$CONEt_2$, etc. as a functional group in a para position has been mainly reported. However, it has been reported that, if the styrene derivative having an electron donating group such as —$CH_3$, —$OCH_3$, —$NH_2$, —$N(CH_3)_2$, etc. as a functional group in a para position is anionically polymerized, the yield of polymerization is decreased due to an addition reaction caused by a strong reactivity of an carbanion or the molecular weight and molecular weight distribution are not controlled. In this case, the functional group should be protected by an appropriate protecting group. That is, the styrene monomer having the functional group such as an amine group, a hydroxy group, a ketone group, a sulfur group, etc. in a para position is protected by the appropriate protecting group such as trimethylsilyl, t-butylmethylsilyl, oxazoline, an ester compound, etc. to be polymerized using the anionic polymerization and then the functional group is separated from the protecting group [Seiichi Nakahama and Akira Hirao, Prog. Polym. Sci., 1990, 15, 299., Akira Hirao, Surapich Loykulnant, Takashi Ishizone, Prog. Polym. Sci., 2002, 15, 299. T. Ishizone, G. Uehara, A. Hirao, and S. Nakahama, Macromolecules, 1998, 31, 3764. T. Ishizone, T. Utaka, Y. Ishino, A. Hirao, and S. Nakahama, Macro-molecules, 1997, 30, 6458, T. Ishizone, G. Uehara, A. Hirao, S. Nakahama, and K. Tsuda, Macromolecules, 1998, 31, 3764.].

Meanwhile, there has been reported a method of anionically polymerizing after reducing the reactivity by forming a complex and coordinately bonding with an additive such as lithium chloride, diethylzinc, dibutylmagnesium, etc. [Christian Schade, Macromol. Chem. Phys., 1999, 200, 621., Y.-S. Cho, J.-S. Lee, Macromol. Rapid Commun. 2001, 22, 8, 638., R. P. Quirk and Y. Lee, J. Polm. Sci. Part A, 2000, 38, 145.].

In a case where the monomer is solid, it is difficult to completely remove impurities existing in the monomer. Accordingly, there occurs a problem in that the activation of an initiator is reduced by the impurities existing in the solid monomer. Moreover, the solubility of the solid monomers becomes an issue in terms of the fact that most anionic polymerizations are typically carried out at low temperatures.

Moreover, there have been reported numerous research results in which complexes are synthesized in the form of a monomer with metal compounds such as iridium using phenylpyridine and phenylpyridine derivatives and then applied to organic electroluminescent elements. Examples of studying energy transfer phenomena using the same have been publicly known in the art. As a relevant prior art, a phenylpyridine is polymerized to form complexes with iridium and various metal compounds and then organic electroluminescent characteristics were measured [L. S. Hung, C. H. Chen, Materials Science and Engineering R, 2002, 39, 143., Maria C. DeRosa, Derek J. Hodgson, Gary D. Enright, Brian Dawson, Christopher E. B. Evans, and Robert J. Crutchley, J. AM. CHEM. SOC., 2004, 126, 7619., Albertus J Sandee, Charlotte K. Williams, Nicholas R. Evans, John E. Davies, Clare E. Boothby, Anna Kohler, Richard H. Friend, and Andrew B. Holmes J. AM. CHEM. SOC., 2004, 126, 7041, M. A. Baldo, S. Lamansky, P. E. Burrows, M. E. Thompson, S. R. Forrest, Appl. Phys. Lett., 75, 4, (1999), Raymond C. Kwong, Sergey Lamansky, and Mark E. Thompson, Adv. Mater., 2000, 12, 1134., K. Dedeian, P. I. Djurovich, F. O. Garces, G. Carlson, R. J. Watts, Inorg. Chem., 1991, 30, 1687-1688., King, K. A, Spellane, P. J., Watts, R. J., J. Am. Chem. Soc., 1985, 107, 1431.].

As described above, most metal complexes containing phenylpyridine are limited to organic monomers. Meanwhile, there has been reported a result of studying electroluminescent characteristics in a manner that vinyl groups are introduced into phenylpyridine to synthesize polymers having side chains of phenylpyridine through a radical polymerization and then complexes are formed with iridium and various metal compounds. Moreover, there has been reported a result of investigating electroluminescent characteristics in a manner that polymers having main chains of phenylpyridine are polymerized through a Suzuki coupling reaction and then complexes are formed with iridium.

Conventional problems such as a phenomenon in which an organic monomer material is decomposed by heat generated from an organic electroluminescent element when an organic monomer is applied to the organic electroluminescent element and an aggregation phenomenon occurring in the material have been solved by introducing a polymer form into an organic metal complex. However, the organic complex in the form of the polymer synthesized by the radical polymerization that is different from the organic monomers having a regular molecular weight showed a decrease in the electroluminescent efficiency due to the irregular molecular weight.

DISCLOSURE OF INVENTION

Technical Problem

Accordingly, the inventors of the present invention have made an effort to prepare a controlled polymer that can be used in the synthesis of an organic metal complex that is widely used as an organic electroluminescent material. As a result, the inventors have confirmed that a novel vinyl-biphenylpyridine monomer having a side chain of pyridine or phenylpyridine as a functional group, a homopolymer having a molecular weight and a molecular weight distribution controlled in such a manner that a side reaction caused by a strong reactivity of an carbanion in the polymerization process of the monomer containing the electron donating group is reduced using an initiator having a low reactivity or by coordinately bonding with an additive, and a block copolymer prepared by polymerizing the vinyl-biphenylpyridine monomer with an aliphatic or aromatic chain group can form complexes with metal compounds as their structures and molecular weights are controlled, and completed the present invention. Accordingly, an object of the present invention is to provide a vinyl-biphenylpyridine monomer, a homopolymer and a block copolymer using the same.

Technical Solution

To accomplish the object of the present invention, there is provided a vinyl-biphenylpyridine monomer represented by the following formula (1):

[Formula 1]

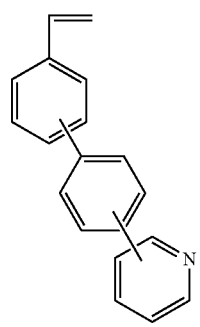

wherein the vinyl-biphenylpyridine monomer includes

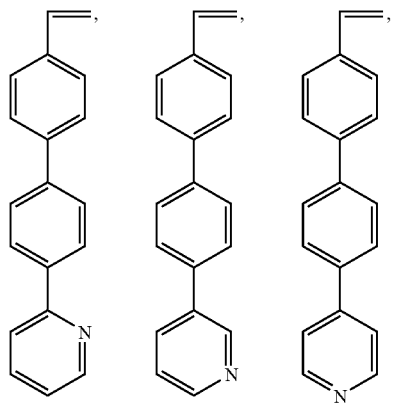

-continued

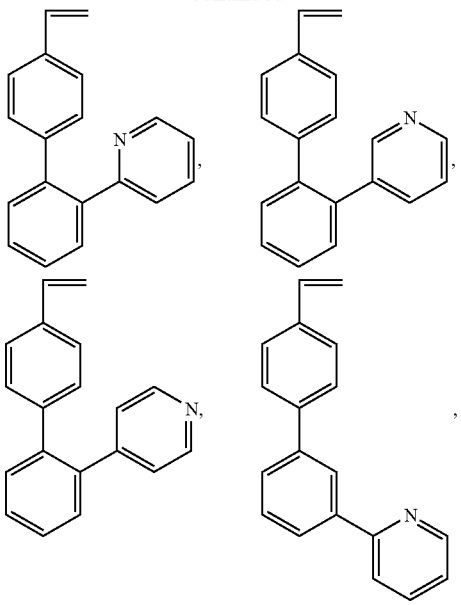

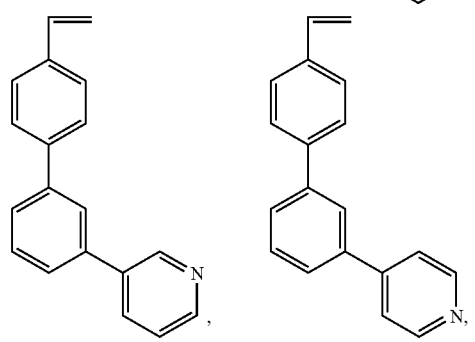

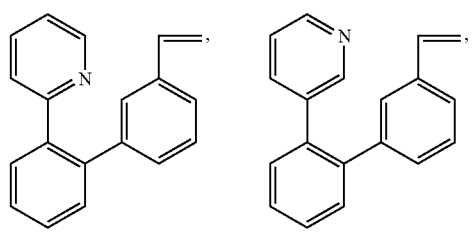

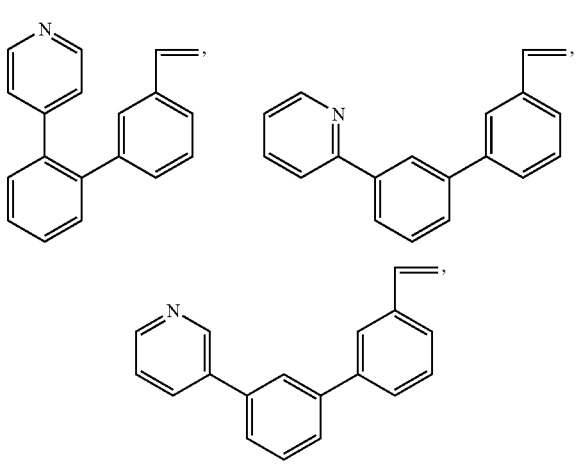

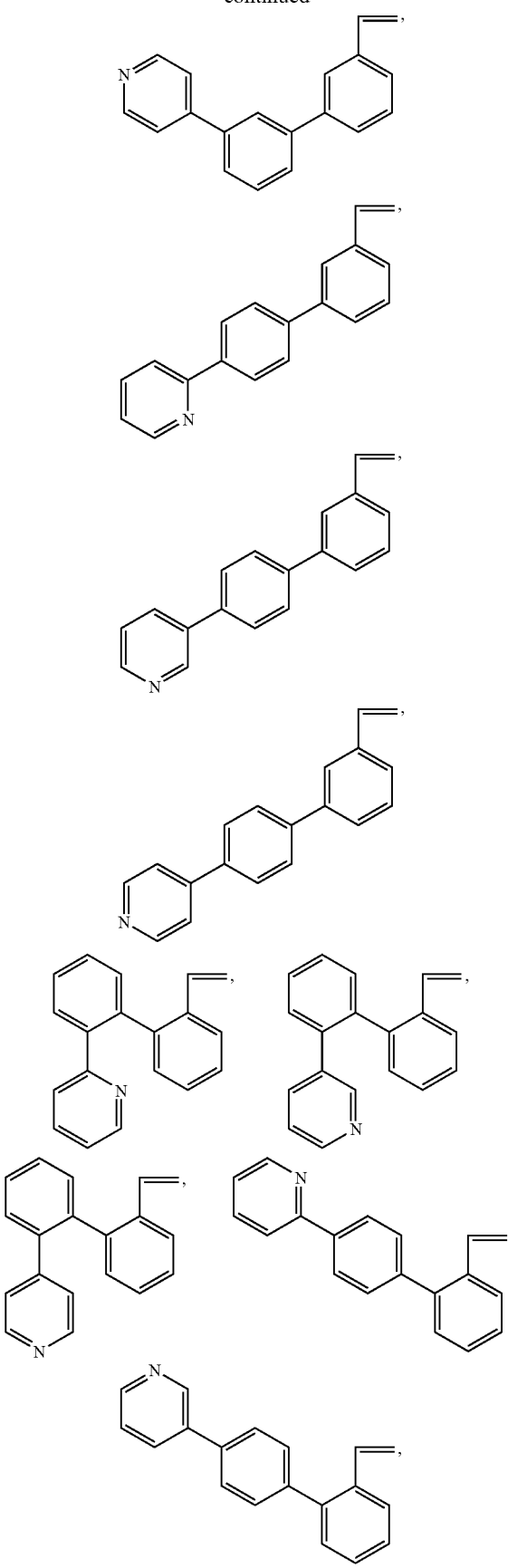

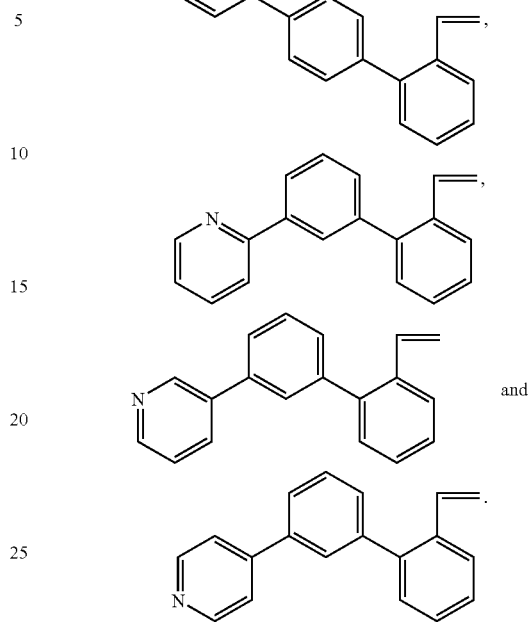

Moreover, another object of the present invention is to provide a method of preparing the vinyl-biphenylpyridine monomer, and the method is represented by the following schemes.

In the first step, a chloro-phenylboronic acid of the following formula (2) and a bromopyridine of the following formula (3) are subjected to a Suzuki coupling reaction in the presence of an alkali metal base and a palladium catalyst, thus preparing a biphenylpyridine of the following formula (4).

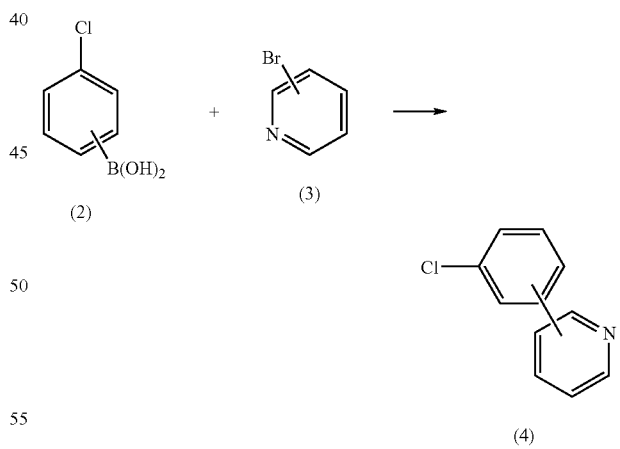

The alkali metal base and palladium catalyst are those commonly used in the art and not limited to particular ones. In more detail, the alkali metal base may be sodium carbonate, potassium carbonate, sodium hydroxide, potassium hydroxide, etc., and the palladium catalyst may be tetrakistriphenylphosphine, palladiumacetate, etc. Here, it is suitable in terms of reaction efficiency that the alkali metal base should be used in a range of 1 to 5 mol % with respect to boronic acid and the palladium catalyst be used in a range of 1 to 3 mol % with respect to the boronic acid As a reaction solvent, tetrahydrofuran (THF), N,N-dimethylformamide (DMF), dimethylsulfoxide (DMSO), toluene, 1,4-dioxane, etc. may be used. It is desirable that the reaction solvent be used in a weight ratio of 10 to 20 with respect to the boronic acid. At this time, the Suzuki coupling reaction is performed in a range of temperatures from 80° C. to 120° C. If the reaction temperature is less than 80° C., the yield may be decreased, whereas, if it exceeds 120° C., an addition reaction may occur.

In the second step, a biphenylpyridine of the following formula (4) and a biphenylboronic acid of the following formula (5) are subjected to the Suzuki coupling reaction in the presence of an alkali metal base and a palladium tetrakistriphenylphosphine catalyst, thus preparing a vinyl-biphenylpyridine of the following formula (1).

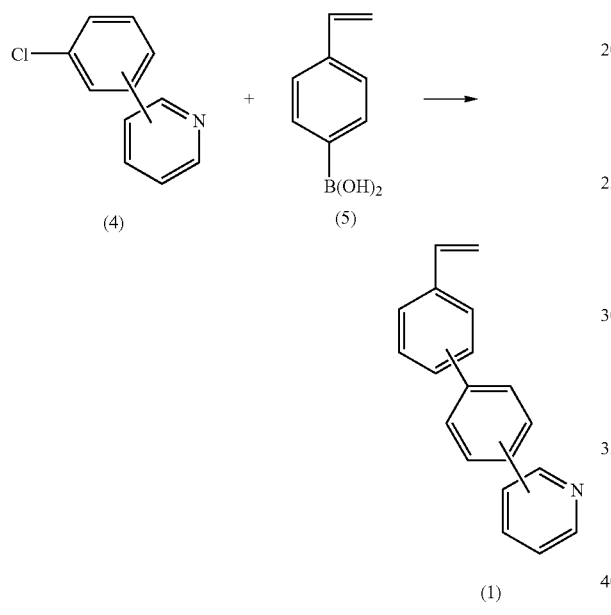

As represented by the following scheme, the vinyl-biphenylpyridine monomer of formula (1) is polymerized through a radical polymerization to prepare a homopolymer having a molecular weight of 100 to 900,000.

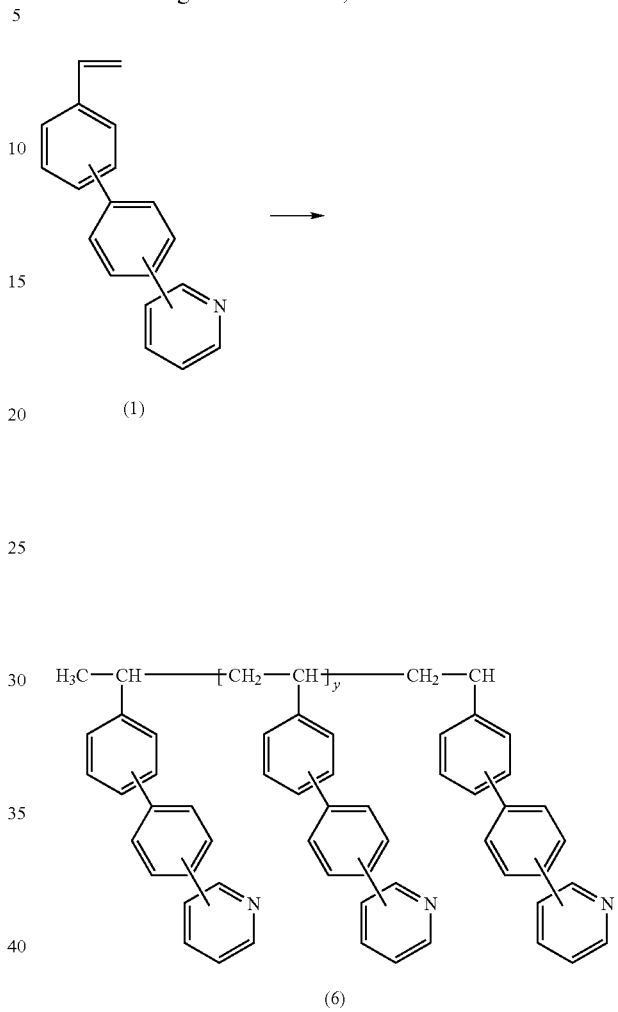

The above reaction is carried out in the presence of the alkali metal base, palladium catalyst and t-butylphosphine [P(t-Bu)$_3$)] commonly used in the art. For example, the alkali metal base may be cesium carbonate, fluoro-potassium, etc., and the palladium catalyst may be palladium tris(dibenzylidene acetone) [Pd$_2$(dba)$_3$], palladiumacetate, etc. As a reaction solvent, tetrahydrofuran (THF), 1,4-dioxane, etc. may be used.

It is desirable in terms of reaction efficiency that the alkali metal base should be used in a range of 1 to 3 wt % with respect to the boronic acid, the palladium catalyst be used in a range of 2 to 5 mol % with respect to the boronic acid, the t-butylphosphine [P(t-Bu)$_3$)] be used in a range of 3 to 6 mol % with respect to the boronic acid, and the reaction solvent be used in a weight ratio of 10 to 20 with respect to the boronic acid. At this time, the Suzuki coupling reaction is performed in a range of temperatures from 80° C. to 120° C. If the reaction temperature is less than 80° C., the yield may be decreased, whereas, if it exceeds 120° C., an addition reaction may occur.

Meanwhile, still another object of the present invention is to provide a polymer prepared using the vinyl-biphenylpyridine.

The radical polymerization is a method commonly used in the art and not limited to a particular one. For example, the present invention performs the radical polymerization in the following manner, but not limited thereto.

An initiator used in the radical polymerization is one that commonly used in the art. For example, an azobisisobutyronitrile (AIBN) initiator or a benzoylperoxide (BPO) initiator is used in a mole range of 0.02 to 0.01 with respect to the monomer. As a solvent that may dissolve the reactant, toluene is used in the present invention. The polymerization reaction is carried out at temperatures from 100° C. to 120° C. for 20 to 30 hours and then methanol is added to a reactor to terminate the reaction. Subsequently, the methanol is removed by filtration, and the polymer is dissolved in benzene and lyophilized to obtain the polymer. The molecular weight and molecular weight distribution of the thus obtained polymer are measured using GPC.

As another method of preparing the homopolymer, the vinyl-biphenylpyridine monomer of the above formula (1) is subjected to an anionic polymerization using potassium-diphenylmethane (K-DPM) as an initiator, as represented by the following scheme:

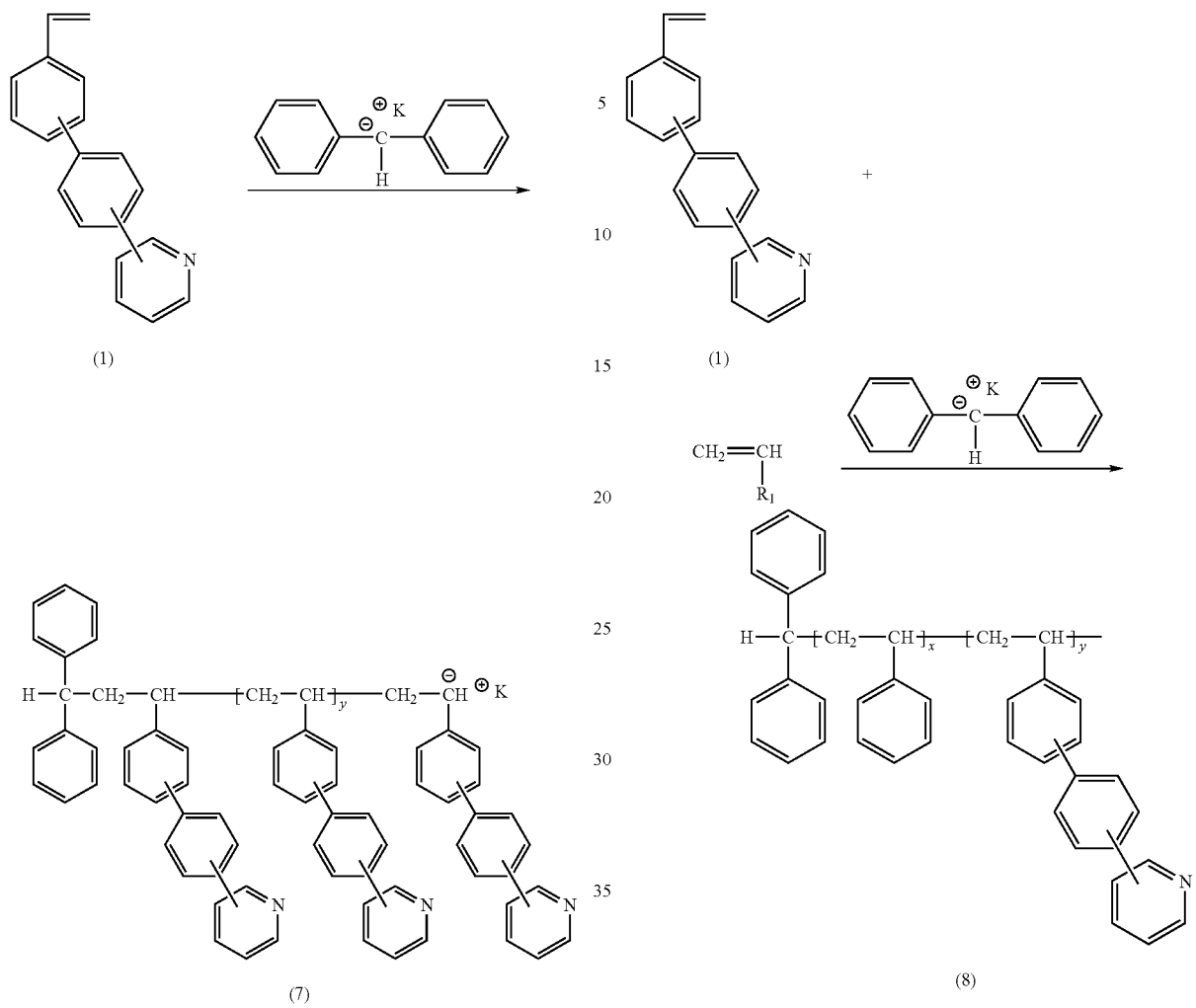

The above anionic polymerization is a method commonly used in the art and not limited to a particular one. For example, the reaction is performed in a glass apparatus under high vacuum using a reaction solvent that may dissolve the reactant, e.g., tetrahydrofuran (THF). First, the potassium-diphenylmethane (K-DPM) initiator is cooled to −30° C. to −90° C., the vinyl-biphenylpyridine monomer is added to be polymerized at 60° C. to −90° C. for 180 to 360 minutes, and then methanol is added to the reactor to terminate the reaction. Subsequently, the methanol is removed by filtration, and the polymer is dissolved in benzene and lyophilized to obtain the polymer. The molecular weight and molecular weight distribution of the thus obtained polymer are measured using GPC and properties thereof are measured through NMR, FT-IR, UV-Vis, etc.

Moreover, the vinyl-biphenylpyridine monomer of formula (1) and a vinyl monomer are subjected to the anion polymerization using the potassium-diphenylmethane (K-DPM) initiator to prepare a block copolymer having a molecular weight of 100 to 900,000.

The block copolymer is one that commonly used in the art and not limited to a particular one. For example, the present invention prepares the block copolymer in the following manner, but not limited thereto. That is, after preparing a homopolymer, a portion of the homopolymer is replaced with the vinyl monomer.

wherein $R_1$ denotes an aliphatic or aromatic chain group.

The above vinyl monomer commonly used in the art has an aromatic unsaturated group. Accordingly, a hydrocarbon compound capable of the polymerization with the monomer represented by the above formula (1) may be applied to a block polymerization. The vinyl monomer used in the preparation of the block copolymer in accordance with the present invention may be styrene, isoprene, 2-vinylpyridine, methylmethacrylate, n-hexylisocyanate and carbazole derivatives. If the styrene is used as the vinyl monomer, it is preferable that the block copolymer be synthesized using a vinyl-phenylpyridine, since the carbanion of the vinyl-phenylpyridine has not a strong reactivity enough to initiate the styrene.

It is desirable that the vinyl-phenylpyridine monomer and the vinyl monomer be used in a range of 10 to 90 wt %, respectively. Moreover, the potassium-diphenylmethane initiator is preferably used in a range of 0.1 to 10 wt % with respect to the vinyl-biphenylpyridine. If the amount used is less than 0.1 wt %, the small amount may not perform the reaction smoothly, whereas, if it exceeds 10 wt %, it has no connection with the reactivity and the amount of the initiator, rather, it is wasteful. Accordingly, it is desirable that the above range be maintained.

BRIEF DESCRIPTION OF THE DRAWINGS

FIG. 1 shows a $^1$H-NMR spectrum of 2-(4-chlorophenyl)pyridine prepared in Example 1 according to the present invention;

FIG. 2 shows a ¹H-NMR spectrum of 2-(4'-vinyl-biphenyl-4-yl)pyridine prepared in Example 10 according to the present invention;

FIG. 3 shows a UV/Vis spectrum of 2-(4'-vinyl-biphenyl-4-yl)pyridine prepared in Example 10 according to the present invention;

FIG. 4 shows a GC/Mass spectrum of 2-(4'-vinyl-biphenyl-4-yl)pyridine prepared in Example 10 according to the present invention;

FIG. 5 shows an FT-IR spectrum of 2-(4'-vinyl-biphenyl-4-yl)pyridine prepared in Example 10 according to the present invention;

FIG. 6 shows a ¹H-NMR spectrum of poly(2-(4'-vinyl-biphenyl-4-yl)pyridine) homopolymer prepared in Example 20 according to the present invention;

FIG. 7 shows a UV/Vis spectrum of poly(2-(4'-vinyl-biphenyl-4-yl)pyridine) homopolymer prepared in Example 20 according to the present invention;

FIG. 8 shows a GPC spectrum of poly(2-(4'-vinyl-biphenyl-4-yl)pyridine) homopolymer prepared in Example 20 according to the present invention;

FIG. 9 shows a DSC spectrum of poly(2-(4'-vinyl-biphenyl-4-yl)pyridine) homopolymer prepared in Example 20 according to the present invention;

FIG. 10 shows a TGA spectrum of poly(2-(4'-vinyl-biphenyl-4-yl)pyridine) homopolymer prepared in Example 20 according to the present invention; and FIG. 11 shows a TGA spectrum of poly(2-(4'-vinyl-biphenyl-4-yl)pyridine)-b-polystyrene block copolymer prepared in Example 21 according to the present invention;

MODE FOR THE INVENTION

Hereinafter, the present invention is described in more detail based on the following Examples. However, the present invention is not limited to the Examples.

Example 1

Preparation of 2-(4-chloro-phenyl)pyridine

Under a nitrogen stream, 5.0 g (0.032 mol) of 4-chloro-phenyl boronic acid, 10.0 g (0.064 mol) of 2-bromopyridine, 150☐ of tetrahydrofuran and 2M potassium carbonate solution (20☐) were placed into a 2-neck round flask 250☐ and then 0.37 g (3 mol %) of palladium tetrakistriphenylphosphine [(pd(PPh$_3$)$_4$] was added as a catalyst. After the resulting solution was heated to reflux at 80° C. for 24 hours, the reaction was terminated. The resulting mixture was poured into a beaker containing 200☐ of distilled water. After extraction with ether (150☐) three times, 10 g of magnesium sulfate was added. The resulting solution was stirred by a rotary stirrer for 30 minutes and then the extraction mixture was filtered. After removing the solvent using a rotary evaporator, the residue was subjected to column chromatography using dichloromethane as a developing solvent and then distilled under reduced pressure to give the 2-(4-chloro-phenyl)pyridine. The yield was 56%.

The ¹H-NHR spectrum is shown in FIG. 1 to confirm the structure of the thus prepared 2-(4-chloro-phenyl)pyridine.

Example 2

Preparation of 3-(4-chloro-phenyl)pyridine

This Example was carried out in the same manner as Example 1, except that 5.0 g (0.032 mol) of 4-chloro-phenyl boronic acid, 10.0 g (0.064 mol) of 3-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 3-(4-chloro-phenyl)pyridine was isolated. The yield was 50%.

Example 3

Preparation of 4-(4-chloro-phenyl)pyridine

This Example was carried out in the same manner as Example 1, except that 5.0 g (0.032 mol) of 4-chloro-phenyl boronic acid, 10.0 g (0.064 mol) of 4-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 4-(4-chloro-phenyl)pyridine was isolated. The yield was 60%.

Example 4

Preparation of 2-(2-chloro-phenyl)pyridine

This Example was carried out in the same manner as Example 1, except that 5.0 g (0.032 mol) of 2-chloro-phenyl boronic acid, 10.0 g (0.064 mol) of 2-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 2-(2-chloro-phenyl)pyridine was isolated. The yield was 50%.

Example 5

Preparation of 3-(2-chloro-phenyl)pyridine

This Example was carried out in the same manner as Example 1, except that 5.0 g (0.032 mol) of 2-chloro-phenyl boronic acid, 10.0 g (0.064 mol) of 3-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 2-(2-chloro-phenyl)pyridine was isolated. The yield was 50%.

Example 6

Preparation of 4-(2-chloro-phenyl)pyridine

This Example was carried out in the same manner as Example 1, except that 5.0 g (0.032 mol) of 2-chloro-phenyl boronic acid, 10.0 g (0.064 mol) of 4-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 4-(2-chloro-phenyl)pyridine was isolated. The yield was 50%.

Example 7

Preparation of 2-(3-chloro-phenyl)pyridine

This Example was carried out in the same manner as Example 1, except that 5.0 g (0.032 mol) of 3-chloro-phenyl boronic acid, 10.0 g (0.064 mol) of 2-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 2-(3-chloro-phenyl)pyridine was isolated. The yield was 55%.

Example 8

Preparation of 3-(3-chloro-phenyl)pyridine

This Example was carried out in the same manner as Example 1, except that 5.0 g (0.032 mol) of 3-chloro-phenyl boronic acid, 10.0 g (0.064 mol) of 3-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 3-(3-chloro-phenyl)pyridine was isolated. The yield was 55%.

Example 9

Preparation of 4-(3-chloro-phenyl)pyridine

This Example was carried out in the same manner as Example 1, except that 5.0 g (0.032 mol) of 3-chloro-phenyl boronic acid, 10.0 g (0.064 mol) of 4-bromopyridine, 150☐ of tetrahydrofuran and 2M potassium carbonate solution (20☐) were added and then 0.37 g (3 mol %) of palladium tetrakistriphenylphosphine [(pd(PPh$_3$)$_4$] was used as a catalyst. Finally, after the resulting solution was heated to reflux at 80° C. for 24 hours, the 3-(3-chloro-phenyl)pyridine was isolated. The yield was 50%.

Example 10

Preparation of 2-(4'-vinyl-biphenyl-4-yl)pyridine

Under a nitrogen stream, 23.42 g (0.158 mol) of 4-vinyl-phenyl boronic acid, 20.0 g (0.1055 mol) of 2-(4-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were placed into a 2-neck round flask 250☐. After the resulting solution was heated to reflux at 80° C. for 24 hours, the reaction was terminated. The resulting mixture was filtered, the catalyst and fluoro-potassium that were black solids were removed, and then the dioxane was removed by rotary evaporation. After extraction with 300☐ of dichloromethane and 400☐ of distilled water, the residue was subjected to column chromatography using a mixed solution of hexane and ethylacetate (7:3) as a developing solvent and then recrystallized at 0° C. using ethylacetate to give the 2-(4'-vinyl-biphenyl-4-yl)pyridine. The yield was 45%. As the structural characteristics of the thus prepared 2-(4'-vinyl-biphenyl-4-yl)pyridine, the $^1$H-NMR spectrum is shown in FIG. 2, the UV/Vis is shown in FIG. 3, the GC-Mass is shown in FIG. 4, and the FT-IR is shown in FIG. 5. Moreover, the analysis data of the 2-(4'-vinyl-biphenyl-4-yl)pyridine is shown in the following table 1:

TABLE 1

| Classification | Nitrogen | Carbon | Hydrogen |
| --- | --- | --- | --- |
| Theoretical Value | 5.44 | 88.68 | 5.88 |
| Measured Value | 5.37 | 89.86 | 5.49 |

Example 11

Preparation of 3-(4'-vinyl-biphenyl-4-yl)pyridine

This Example was carried out in the same manner as Example 10, except that 23.42 g (0.158 mol) of 4-vinyl-phenyl boronic acid, 20.0 g (0.1055 mol) of 3-(4-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 3-(4'-vinyl-biphenyl-4-yl)pyridine was isolated. The yield was 47%.

Example 12

Preparation of 4-(4'-vinyl-biphenyl-4-yl)pyridine

This Example was carried out in the same manner as Example 10, except that 23.42 g (0.158 mol) of 4-vinyl-phenyl boronic acid, 20.0 g (0.1055 mol) of 4-(4-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 4-(4'-vinyl-biphenyl-4-yl)pyridine was isolated. The yield was 50%.

Example 13

Preparation of 2-(4'-vinyl-biphenyl-2-yl)pyridine

This Example was carried out in the same manner as Example 10, except that 23.42 g (0.158 mol) of 4-vinyl-phenyl boronic acid, 20.0 g (0.1055 mol) of 2-(2-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 2-(4'-vinyl-biphenyl-2-yl)pyridine was isolated. The yield was 50%.

Example 14

Preparation of 3-(4'-vinyl-biphenyl-2-yl)pyridine

This Example was carried out in the same manner as Example 10, except that 23.42 g (0.158 mol) of 4-vinyl-phenyl boronic acid, 20.0 g (0.1055 mol) of 3-(2-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 3-(4'-vinyl-biphenyl-2-yl)pyridine was isolated. The yield was 50%.

Example 15

Preparation of 4-(4'-vinyl-biphenyl-2-yl)pyridine

This Example was carried out in the same manner as Example 10, except that 23.42 g (0.158 mol) of 4-vinyl-phenyl boronic acid, 20.0 g (0.1055 mol) of 4-(2-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P(t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 4-(4'-vinyl-biphenyl-2-yl)pyridine was isolated. The yield was 42%.

Example 16

Preparation of 2-(4'-vinyl-biphenyl-3-yl)pyridine

This Example was carried out in the same manner as Example 10, except that 23.42 g (0.158 mol) of 4-vinyl-phenyl boronic acid, 20.0 g (0.1055 mol) of 2-(3-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P( t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 2-(4'-vinyl-biphenyl-3-yl)pyridine was isolated. The yield was 45%.

Example 17

Preparation of 3-(4'-vinyl-biphenyl-3-yl)pyridine

This Example was carried out in the same manner as Example 10, except that 23.42 g (0.158 mol) of 4-vinyl-phenyl boronic acid, 20.0 g (0.1055 mol) of 3-(3-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P( t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 3-(4'-vinyl-biphenyl-3-yl)pyridine was isolated. The yield was 45%.

Example 18

Preparation of 4-(4'-vinyl-biphenyl-3-yl)pyridine

This Example was carried out in the same manner as Example 10, except that 23.42 g (0.158 mol) of 4-vinyl-phenyl boronic acid, 20.0 g (0.1055 mol) of 4-(3-chloro-phenyl)pyridine, 500☐ of 1,4-dioxane, 27.54 g (0.474 mol, 3.3 equivalent) of fluoro-potassium, 1.69 g (0.0084 mol, 5.3 mol %) of t-butylphosphine [P( t-Bu)$_3$)], and 2.6 g (0.0028 mol, 1.8 mol %) of palladium tris(dibenzylidene acetone) [Pd$_2$(dba)$_3$] were used. Finally, after the resulting solution was heated to reflux at 80° C. for 24 hours, the 4-(4'-vinyl-biphenyl-3-yl)pyridine was isolated. The yield was 48%.

Example 19

Preparation of poly(2-(4'-vinyl-biphenyl-4-yl)pyridine Homopolymer by Radical Polymerization 2-(4'-vinyl-biphenyl-4-yl)pyridine monomer was subjected to a radical polymerization to synthesize a homopolymer in the following synthesis process.

2.0 g of 2-(4'-vinyl-biphenyl-4-yl)pyridine monomer and 0.05 g of azobisisobutyronitrile (AIBN) initiator (or 0.038 g of benzoylperoxide (BPO)) were added to 10☐ of toluene. After polymerizing the resulting solution at 110° C. for 24 hours, methanol was added to the reactor to terminate the reaction. Subsequently, the methanol was removed by filtration, and the polymer was dissolved in benzene and lyophilized to obtain the polymer. The yield of the thus obtained polymer was 100%, the molecular weight was 36,000, and the molecular weight distribution was 1.86.

Example 20

Preparation of poly(2-(4'-vinyl-biphenyl-4-yl)pyridine homopolymer

As shown in the following table 2, a homopolymerization was performed using a glass apparatus under high vacuum. Tetrahydrofuran (THF) was used as a solvent. A potassium-diphenylmethane (K-DPM) initiator was cooled to −78° C., a 2-(4'vinyl-biphenyl-2-yl)pyridine monomer was added to be polymerized at −78° C. for 30 to 150 minutes, and then methanol was added to the reactor to terminate the reaction. Subsequently, the methanol was removed by filtration, and the polymer was dissolved in benzene and lyophilized to obtain the polymer. The molecular weight and molecular weight distribution of the thus obtained polymer were measured using GPC.

TABLE 2

| Example 20 | Reactant(mmol) | | Reaction Time(Min) | Polymer | | | Yield (%) |
| | | | | Number Average Molecular Weight($10^{-3}$) | | | |
| | K-DPM | VPPPy | | Calculated Value | Measured Value | Mw/Mn | |
| --- | --- | --- | --- | --- | --- | --- | --- |
| 1 | 0.0920 | 3.10 | 180 | 8.0 | 10.2 | 1.06 | 48.0 |
| 2 | 0.0413 | 2.92 | 300 | 16.5 | 18.2 | 1.26 | 90.7 |
| 3 | 0.05571 | 2.50 | 360 | 11.5 | 12.2 | 1.25 | 100 |

K-DPM: Potassium-diphenylmethane; VPPPy: Vinyl-phenylpyridine; Mw: Weight average molecular weight; and Mn: Number average molecular weight

Example 21

Preparation of 2-(4'-vinyl-biphenyl-4-yl)pyridine block copolymer

As shown in the following table 3, the synthesis of the block copolymer was carried out by synthesizing the homopolymer in the same manner as described above and then by replacing a portion of the homopolymer with the second monomer at −78° C. The monomers used in the synthesis processes of the vinyl-phenylpyridine and the block copolymer were styrene, isoprene, 2-vinylpyridine, methylmethacrylate, n-hexylisocyanate, etc. Here, in the case where the styrene and isoprene were used, the block copolymer was synthesized using vinyl-phenylpyridine as the second monomer, since the carbanion of the vinyl-phenylpyridine had not a strong reactivity enough to initiate the styrene and isoprene.

TABLE 3

| Example | Reactant(mmol) | | | Time (Min) | Block Copolymer Number Average Molecular Weight($10^{-3}$) | | Mw/Mn | Yield (%) |
|---|---|---|---|---|---|---|---|---|
| 24 | K-DPM | Monomer 1 | Monomer 2 | | Calculated Value | Measured Value1 | | |
| 1 | 0.059 | St(4.69) | VPPPy(2.60) | 390 | 19.5(8.2) | 23.9(7.0) | 1.07(1.40) | 100 |
| 2 | 0.0504 | 2VP(4.70) | VPPPy(2.55) | 390 | 22.9(9.9) | 32.5(9.3) | 1.08(1.10) | 100 |

K-DPM: Potassium-diphenylmethane; St: Styrene; 2VP: 2-vinylpyridine; VPPPy: Vinyl-phenylpyridine; Mw: Weight average molecular weight; and Mn: Number average molecular weight

INDUSTRIAL APPLICABILITY

According to the present invention, as the structures and molecular weights of a novel vinyl-biphenylpyridine monomer having a side chain of pyridine or phenylpyridine as a functional group, a homopolymer having a molecular weight and a molecular weight distribution controlled in such a manner that a side reaction caused by a strong reactivity of an carbanion in the polymerization process of the monomer containing the electron donating group is reduced using an initiator having a low reactivity or by coordinately bonding with an additive, and a block copolymer prepared by polymerizing the vinyl-biphenylpyridine monomer with an aliphatic or aromatic chain group can be controlled to form complexes with metal compounds, their application range is expected to be expanded as nano and optical functional materials.

The invention claimed is:

1. A vinyl-biphenyl pyridine monomer represented by the following formula (1):

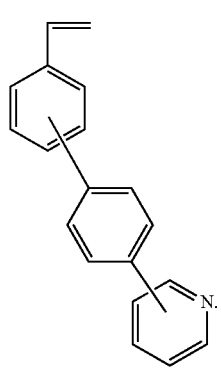

2. A method of preparing a vinyl-biphenylpyridine monomer comprising:

(i) preparing a (chloro-phenyl)pyridine of the following formula (4) by subjecting a chloro-phenylboronic acid of the following formula (2) and a bromopyridine of the following formula (3) to a Suzuki coupling reaction in the presence of an alkali metal base and a palladium catalyst,

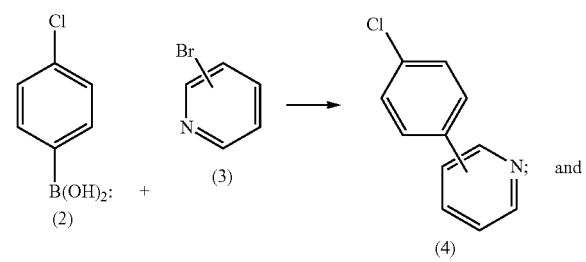

(ii) preparing a vinyl-biphenylpyridine of the following formula (1) by subjecting a (chloro-phenyl)pyridine of the following formula (4) and a vinyl-phenylboronic acid of the following formula (5) to the Suzuki coupling reaction in the presence of an alkali metal base and a palladium tetrakistriphenylphosphine catalyst,

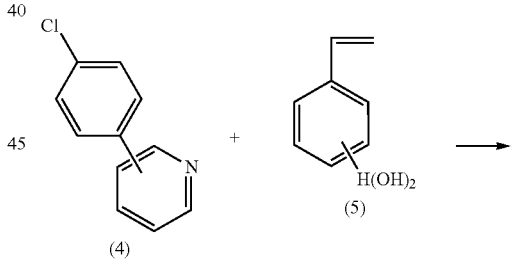

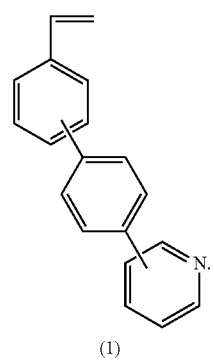

3. A vinyl-biphenylpyridine homopolymer, prepared by polymerizing a vinyl-biphenylpyridine monomer of the following formula (1), having a molecular weight of 100 to 900,000:

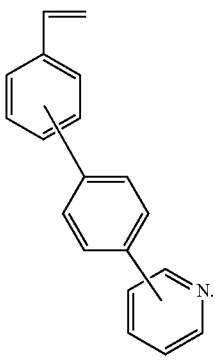

[Formula 1]

4. A vinyl-biphenylpyridine block copolymer, prepared by polymerizing a vinyl-biphenylpyridine monomer of the following formula (1) and a vinyl monomer, having a molecular weight of 100 to 900,000:

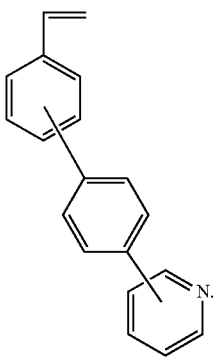

[Formula 1]

5. The block copolymer of claim 4, wherein the vinyl monomer is one selected from the group consisting of styrene, isoprene, 2-vinylpyridine, methylmethacrylate, n-hexylisocyanate and carbazole derivatives.

6. A method of preparing a vinyl-biphenylpyridine homopolymer having a molecular weight of 100 to 900,000 by subjecting a vinyl-biphenylpyridine monomer of the following formula (1) to a radical polymerization:

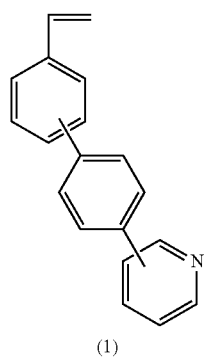

(1) 

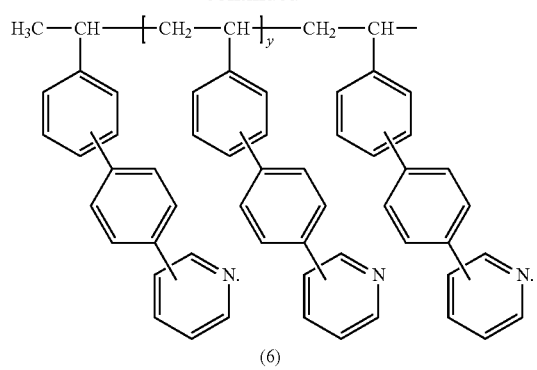

(6)

7. A method of preparing a vinyl-biphenylpyridine homopolymer having a molecular weight of 100 to 900,000 by subjecting a vinyl-biphenylpyridine monomer of the following formula (1) to an anionic polymerization using a potassium-diphenylmethane initiator:

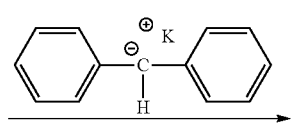

(1)

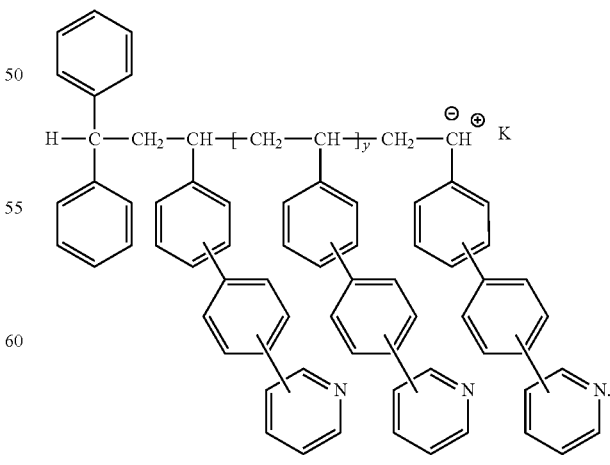

(7)

8. A method of preparing a vinyl-biphenylpyridine block copolymer having a molecular weight of 100 to 900,000 by subjecting 10 to 90 wt % of a vinyl-biphenylpyridine monomer of the following formula (1) and 10 to 90 wt % of a vinyl monomer to an anionic polymerization in the presence of a potassium-diphenylmethane initiator:
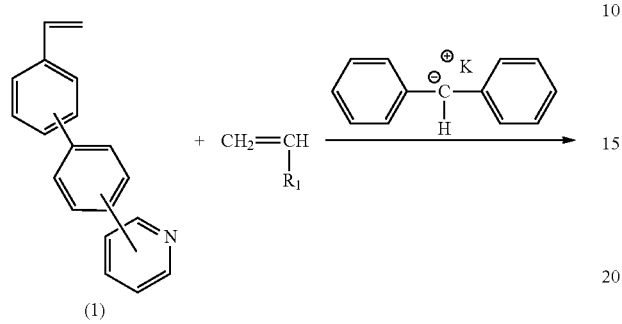
(1)
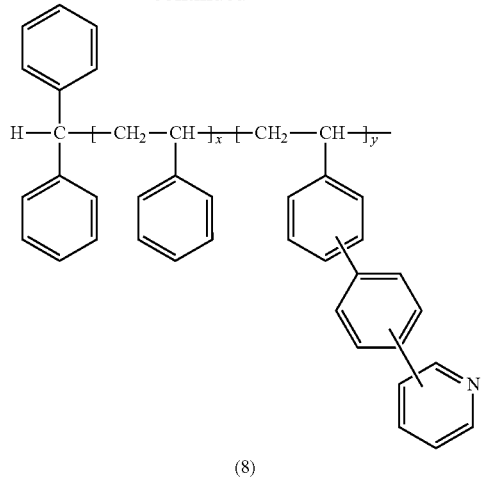
(8)
wherein $R_1$ denotes an aliphatic or aromatic chain group.
* * * * *